United States Patent
Zhang et al.

(10) Patent No.: US 6,844,552 B2
(45) Date of Patent: Jan. 18, 2005

(54) TERAHERTZ TRANSCEIVERS AND METHODS FOR EMISSION AND DETECTION OF TERAHERTZ PULSES USING SUCH TRANSCEIVERS

(75) Inventors: Xi-Cheng Zhang, Latham, NY (US); Masahiko Tani, Himeji (JP); Zhiping Jiang, Ottawa (CA); Qin Chen, Emmaus, PA (US)

(73) Assignee: Rensselaer Polytechnic Institute, Troy, NY (US)

( * ) Notice: Subject to any disclaimer, the term of this patent is extended or adjusted under 35 U.S.C. 154(b) by 276 days.

(21) Appl. No.: 09/826,458

(22) Filed: Apr. 5, 2001

(65) Prior Publication Data

US 2001/0038074 A1 Nov. 8, 2001

Related U.S. Application Data

(60) Provisional application No. 60/195,708, filed on Apr. 7, 2000, and provisional application No. 60/195,554, filed on Apr. 6, 2000.

(51) Int. Cl.$^7$ ................................................. G01J 5/02
(52) U.S. Cl. ............................. 250/338.1; 250/341.8; 324/639
(58) Field of Search ........................... 250/338.1, 341.8; 324/639

(56) References Cited

U.S. PATENT DOCUMENTS

| | | | |
|---|---|---|---|
| 3,824,717 A | 7/1974 | Evtuhov et al. | 307/88.3 |
| 4,510,402 A | 4/1985 | Summers et al. | 307/427 |
| 4,755,820 A | 7/1988 | Backhouse et al. | 343/700 MS |
| 4,757,268 A | 7/1988 | Abrams et al. | 330/4.3 |
| 4,759,820 A | 7/1988 | Calvert et al. | 156/600 |
| 4,896,942 A | * 1/1990 | Onstott et al. | 385/127 |
| 4,922,091 A | 5/1990 | Grischkowsky | 250/211 J |
| 5,144,630 A | 9/1992 | Lin | 372/22 |
| 5,332,918 A | 7/1994 | Smith et al. | 257/431 |
| 5,355,247 A | 10/1994 | Byer et al. | 359/330 |
| 5,377,043 A | 12/1994 | Pelouch et al. | 359/326 |

(List continued on next page.)

FOREIGN PATENT DOCUMENTS

| | | |
|---|---|---|
| DE | 196 29 583 | 1/1998 |
| EP | 0 828 143 | 3/1998 |

OTHER PUBLICATIONS

M. Tani et al., "Photoconductive Terahertz Transceivers," Electronics Letters, vol. 36, No. 9, pp. 804–805 (Apr. 27, 2000).

(List continued on next page.)

*Primary Examiner*—Constantine Hannaher
*Assistant Examiner*—Shun Lee
(74) *Attorney, Agent, or Firm*—RatnerPrestia

(57) ABSTRACT

A system for emitting and detecting terahertz frequency electromagnetic pulses. The system comprises a single transceiver device, which may be an electro-optic crystal or photoconductive antenna, for both emitting and detecting the pulses. A related method comprises using a single transceiver device to both emit and detect electromagnetic terahertz frequency pulses. The transceiver device is excited by a pump pulse to emit a terahertz output pulse, which is modulated with a chopper. An object reflects the terahertz pulse and the reflected pulse is detected in the transceiver using a probe pulse. A lock-in amplifier set to the same frequency of the chopper is used to reduce noise in the signal detected by the transceiver. An image of the object may be created using the intensity or the timing of the peak amplitude of the terahertz pulses reflected from the object.

24 Claims, 5 Drawing Sheets

U.S. PATENT DOCUMENTS

| | | | |
|---|---|---|---|
| 5,493,719 A | 2/1996 | Smith et al. | 455/325 |
| 5,543,960 A | 8/1996 | Carrig et al. | 359/326 |
| 5,663,639 A | 9/1997 | Brown et al. | 324/96 |
| 5,729,017 A | 3/1998 | Brener et al. | 250/338.1 |
| 5,789,750 A | 8/1998 | Nuss | 250/338.1 |
| 5,844,288 A | 12/1998 | Mourou et al. | 257/431 |
| 5,894,125 A | 4/1999 | Brener et al. | 250/330 |
| 5,937,118 A | 8/1999 | Komori | 385/27 |
| 5,946,085 A | 8/1999 | Kawashima et al. | 356/28 |
| 5,952,818 A | 9/1999 | Zhang et al. | |
| 6,014,249 A | 1/2000 | Fermann et al. | 359/341 |
| 6,038,060 A | 3/2000 | Crowley | 359/328 |
| 6,078,047 A | 6/2000 | Mittleman et al. | 250/338.1 |
| 6,111,416 A | 8/2000 | Zhang et al. | 324/753 |
| 6,144,679 A | 11/2000 | Herman et al. | 372/21 |
| 6,239,866 B1 * | 5/2001 | Bromage et al. | 356/5.01 |
| 6,275,045 B1 * | 8/2001 | Eloy | 324/639 |

OTHER PUBLICATIONS

Q. Chen et al., "Electro–Optic Terahertz Transceiver," Electronics Letters, vol. 36, No. 15, pp. 1298–1299 (Jul. 20, 2000).

Q. Chen et al., "Electro–Optic Transceivers for Terahertz–Wave Applications," J. Opt. Soc. Am. B., vol. 18, No. 6, pp. 823–831 (Jun. 2001).

International Search Report dated Sep. 6, 2001.

Q. Chen, P. Y. Han, Z. Jiang, X.–C. Zhang, "Recent Development of Free–Space $TH_z$ Imaging," Invited Paper, The 7th International Conference on Terhertz Electronics, Nara, Japan, Nov. 1999 (4 pages).

Q. Wu et al., "Free–space Electro–Optic Sampling of Terahertz Beams," Appl. Phys. Lett. 67, 3523 (1995).

Q. Wu et al., "Ultrafast Electro–Optic Field Sensors," Appl. Phys. Lett. 68, 1604 (1996).

Q. Wu et al., "Broadband Detection Capability of ZnTe Electro–Optic Field Detectors," Appl. Phys Lett 68, 2924 (1996).

Q Wu et al, Dynamic Range of an Electro–Optic Field Sensor and Its Imaging Applications, Appl. Pys. Lett 68, 3224 (1996).

Q. Wu et al., Two–Dimensional Electro–Optic Imaging of $TH_z$ Beams, Appl. Phys. Lett. 69, 1026 (1996).

Q. Wu et. al, "7 Terahertz Broadband GaP Electro–Optic Sensor," Appl. Phys. Lett. 70, 1784 (1997).

P. hd Jepsen et al, "Detection of $H_z$ Pulses by Phase Retardation in Lithium Tantalate," Phys. Rev. E. 53,3052 (1996).

Nahata et al., "Coherent Detection of Freely Propagating Terahertz Radiation by Electro–Optic Sampling," Appl. Phys. Lett. 68, 150 (1996).

Nahata et al., Reshaping of Freely Propagating Terahertz Pulses by Diffraction, IEEE–JSTQE, 701 (1996), vol. 2, No. 3.

X.–C. Zhang and Q. Wu. "New Terahertz Beams Imaging Device," Optics & Photonics News, 12, 9 (1996).

X.–C. Zhang, Q. Wu, and T. D. Hewitt, "Electro–Optic Imaging of Terahertz Beams," Ultrafast Phenomena X, Springer Series in Chemical Physics, 54 (1996).

Z. G. Lu, P. Campbell, and X.–C. Zhang, "Free Space Electro–Optic Sampling With a High–Repetition–Rate Regenerative Amplified Laser," Appl. Phys. Lett., 71, 593 (1997).

Zhiping Jiang, F. G. Sun, Q. Chen, and X.–C. Zhang, "Electro–Optic Sampling Near Zero Optical Transmission Point," Appl. Phys. Lett., 74, 1191 (1999).

Y. Cai et al., "Coherent Terahertz Radiation Detection: Direct Comparison Between Free–Space Electro–Optic Sampling and Antenna Detection," Appl. Phys. Lett., 73, 444 (1998).

Q. Wu and X.–C. Zhang, "Design and Characterization of Traveling Wave Electro–Optic Terahertz Sensors," IEEE J. Sel. Top. Quantum Electron, 2, 693 (1996).

C. Winnewisser et al., "Electro–Optic Detection of THz Radiation in $LiTaO_3$, $LiNbO_3$ and ZnTe," Appl. Phys. Lett., 70, 3069 (1997).

A. Nahata, A. Weling, and T. Heinz, "A Wideband Coherent Terahertz Spectroscopy System Using Optical Rectification and Electro–Optic Sampling," Appl. Phys. Lett., 69, 2321 (1996).

G. Mourou et al., "Picosecond Microwave Pulse Generation," Appl. Phys. Lett., 38, 470 (1981).

D. H. Auston et al., "Picosecond Photoconducting Hertzian Dipoles," Appl. Phys. Lett., 45, 284 (1984).

A. P. DeFonzo, M. Jarwala, and C. R. Lutz, "Transient Response of Planar Integrated Optoelectronic Antennas." Appl. Phys. Lett., 50, 1155 (1987).

Ch. Fattinger and D. Grischkowsky, "Point Source Terahertz Optics," Appl. Phys. Lett., 53, 1480 (1988).

P. R. Smith, D. H. Auston, and M. C. Nuss, "Subpicosecond Photoconducting Dipole Antennas," IEEE J. Quantum Electron, 24, 255 (1988).

B. B. Hu and M. C. Nuss, "Imaging With Terahertz Waves," Opt. Lett., 20, 1716 (1995).

R. A. Cheville, D. Grischkowsky, "Time Domain Terahertz Impulse Ranging Studies," Appl. Phys. Lett., 67, 1960 (1995).

D. M. Mittleman et al., "T–Ray Tomography," Opt. Lett., 22, 904 (1997).

D. Mittleman et al., "T–Ray Imaging," IEEE J. Sel. Top. Quantum Electron, 2, 679 (1996).

A. Nahata et al., "High–speed Electrical Sampling Using Optical Second–Harmonic Generation," Appl. Phys. Lett. 69, 746 (1996).

D. Grischkowsky et al., "Far–Infrared Time–Domain Spectroscopy With Terahertz Beams of Dielectrics and Semiconductors," J. Opt. Soc. Am. B., 7, 2006 (1990).

* cited by examiner

Time (ps)

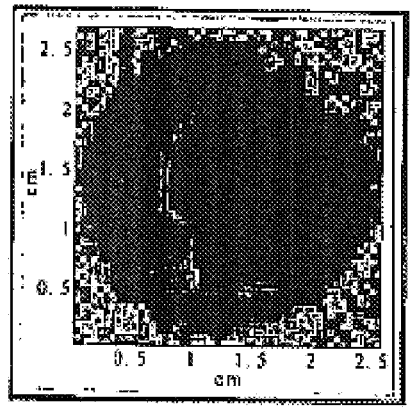
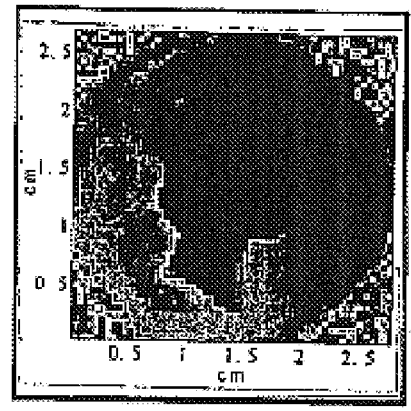
Fig. 10A　　　　　　　　Fig. 10B
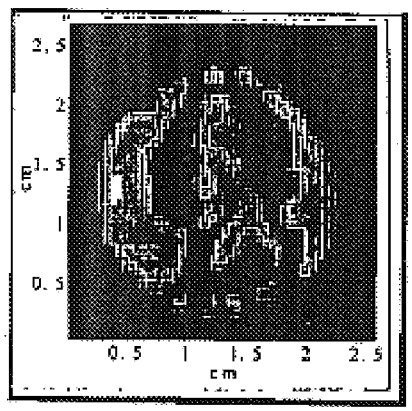
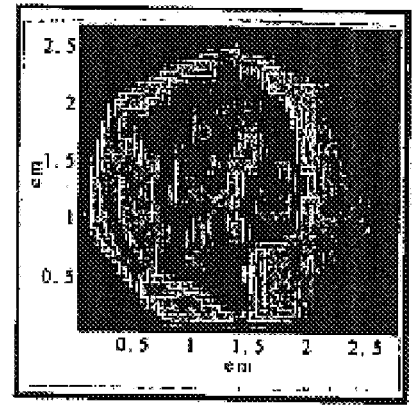
Fig. 11A　　　　　　　　Fig. 11B

TERAHERTZ TRANSCEIVERS AND METHODS FOR EMISSION AND DETECTION OF TERAHERTZ PULSES USING SUCH TRANSCEIVERS

CROSS-REFERENCE TO RELATED APPLICATIONS

This application claims priority based upon U.S. Provisional Patent Application Ser. No. 60/195,554, filed on Apr. 6, 2000, and U.S. Provisional Patent Application Ser. No. 60/195,708, filed on Apr. 7, 2000, both of which are incorporated by reference.

TECHNICAL FIELD

The present invention relates generally to the emission and detection of electromagnetic pulses and, more specifically, to transceivers for use in the terahertz (THz) frequency range.

BACKGROUND OF THE INVENTION

Electro-optic crystals and photoconductive dipole antennas have been widely used in terahertz (THz) time-domain spectroscopy and related imaging applications. For example, U.S. Pat. No. 5,952,818, issued to Zhang et al., discloses an electro-optical sensing apparatus and method for characterizing free-space electromagnetic radiation suitable for real-time, two-dimensional, far-infrared imaging applications. Pulsed terahertz electromagnetic radiation illuminates the electro-optical crystal, modulating the index of refraction via the Pockels effect. A femtosecond optical pulse probes the field-induced change in the index of refraction by passing through the crystal. To convert the field-induced ellipticity modulation in the probe pulse into an intensity modulation, the probe pulse is analyzed by a compensator and polarizer, and detected by a photodetector.

U.S. Pat. No. 5,789,750, issued to Nuss, discusses the use of a photoconductive dipole antenna structure usable as either a terahertz transmitter or a terahertz detector. U.S. Pat. No. 6,078,047, issued to Mittleman et al., discloses a method and apparatus for terahertz tomographic imaging, the apparatus including a photoconductive terahertz transmitter that generates terahertz radiation for illuminating a test object, and a separate photoconductive terahertz detector for detecting pulses reflected by the object. Measurement of the relative time delays of pulses reflected by the object are used to determine the positions of dielectric interfaces in the object.

In the standard apparatus used for THz time-domain spectroscopy as described in the above patents and elsewhere in the art, however, a separate transmitter and receiver are used for the emission and detection of the THz signal. Because detection is the reverse process of emission, the transmitter and the receiver can be identical devices. Despite advantages to be gained by using a single device as both a transmitter and a receiver (a "transceiver"), terahertz transceivers have not previously been known or used in the art, primarily because of perceived technical hurdles and inherent complexity, such as the difficulty of providing an acceptable signal-to-noise ratio.

SUMMARY OF THE INVENTION

The present invention comprises a system for emitting and detecting terahertz frequency electromagnetic pulses. The system has a single transceiver device for both emitting and detecting the pulses. In particular, the device may be an electro-optic crystal or a photoconductive antenna.

In one embodiment, the system further comprises an optical source and related optics for providing a plurality of pump pulses to excite the transceiver to emit a corresponding plurality of terahertz output pulses and a plurality of probe pulses. A chopper modulates the terahertz output pulses at a first frequency. An object is illuminated by the modulated terahertz output pulses and reflects the plurality of modulated terahertz output pulses. The probe pulses are timed to illuminate the transceiver simultaneously with a corresponding plurality of reflected terahertz pulses. A lock-in amplifier, having its reference input connected to the clock output of the chopper, receives a plurality of electrical signals carrying information proportional to the corresponding reflected terahertz pulses detected by the transceiver. The use of the synchronized chopper and lock-in amplifier allows the lock-in amplifier to reduce noise in the signals.

In one embodiment, a miniature electro-optic crystal may be mounted to the end of an optical fiber. The miniature electro-optic crystal may have a volume, for example, of less than about 1 mm$^3$. The optical fiber may be a polarization-preserved optical fiber.

The invention also comprises a method for emitting and detecting terahertz frequency electromagnetic pulses. The method includes the step of emitting and detecting the terahertz frequency electromagnetic pulses with a single transceiver device. The method may further include exciting the transceiver device with a pump pulse to emit a first terahertz frequency output pulse. The terahertz frequency output pulse is modulated with a chopper set at a first frequency. An object is illuminated with the modulated terahertz frequency output pulse, the object reflecting a reflected terahertz pulse. A transceiver device is illuminated with the reflected terahertz pulse simultaneously as a probe pulse illuminates the transceiver device, such that the transceiver device produces a first signal carrying information from the reflected terahertz pulse.

If the transceiver device is an electro-optic crystal, the terahertz pulse modulates the probe pulse in the electro-optic crystal and the electro-optic crystal reflects the modulated probe pulse from a back surface of the electro-optic crystal. The first signal comprises the reflected, modulated probe pulse. In such a case, the method further comprises detecting the reflected, modulated probe pulse with a photodetector; converting the information to a second signal; and reducing noise in the second signal with a lock-in amplifier to produce a third, noise-reduced signal.

If the transceiver device is a photoconductive antenna, the method may include creating through the terahertz pulse and the probe pulse a current in the antenna comprising the first signal. The method further includes reducing noise in the first signal with a lock-in amplifier to produce a second, noise-reduced signal.

The object may have a plurality of layers, each layer a different distance from the transceiver. The method may further comprise generating a plurality of pump pulses, probe pulses, and terahertz pulses such that the object reflects a plurality of corresponding reflected terahertz pulses, each pulse having a peak amplitude intensity and a peak amplitude timing that corresponds to the distance from the transceiver of the layer that reflected the pulse. A tomographic image of the object may then be created using the peak amplitude intensity or the peak amplitude timing.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 10A is an image of an American quarter dollar generated using an exemplary embodiment of the present invention, where the gray level represents the timing of the peak amplitude;

FIG. 10B is an image of a British fifty pence piece generated using an exemplary embodiment of the present invention, where the gray level represents the timing of the peak amplitude;

FIG. 11A is an image of an American quarter dollar generated using an exemplary embodiment of the present invention, where the gray level represents the peak amplitude within a certain timing window;

FIG. 11B is an image of a British fifty pence piece generated using an exemplary embodiment of the present invention, where the gray level represents the peak amplitude within a certain timing window.

DETAILED DESCRIPTION OF INVENTION

Unlike the conventional setup in which the THz transmitter and receiver are spatially and functionally separate devices, the THz transceiver of the present invention combines two functions into one device. The THz transceiver alternately transmits pulsed electromagnetic radiation at a THz frequency and receives the returned signal. The THz transceiver may comprise an electro-optic crystal or a photoconductive antenna. For an electro-optic crystal transceiver, the electromagnetic radiation is optically rectified and the returned optical signal is received by the crystal via the electro-optic effect using femtosecond optics. In both the electro-optic crystal and photoconductive antenna embodiments, the system complexity is greatly reduced by using only a single transceiver instead of a separate emitter and receiver.

Figure 12:
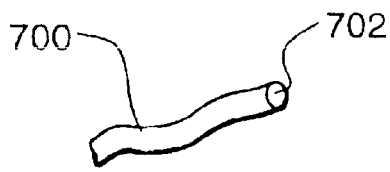
FIG. 12 illustrates an exemplary optical fiber THz transceiver.

A performance comparison of the photoconductive transceiver embodiment and the electro-optic transceiver embodiment is similar to any comparison of a photoconductive method versus an electro-optic method using separate THz transmitters and detectors. Electro-optic transceivers typically require more optical power than photoconductive antennas, but have a lower signal-to-noise ratio at low frequency. Electro-optic transceivers typically have broader bandwidth than a photoconductive antenna and offer the potential for a smaller-sized transceiver, in part because electro-optic crystal embodiments do not have the amount of wiring and packaging typical of photoconductive antenna embodiments. As shown in FIG. 12, a miniature electro-optic crystal transceiver 700, for example having a volume of less than about 1 mm$^3$, may be attached at the end of a polarization-preserved optical fiber 702, providing a true optical fiber THz transceiver.

Configurations for using THz transceivers are less complex than conventional THz systems using two antennas or crystals and two parabolic mirrors. Having a single transceiver also simplifies alignment of the optics. THz transceivers may have unique applications in THz ranging and THz sensing, and may be particularly ideal for THz imaging and tomography in reflection configurations. Along with the use of ultrafast fiber laser and optical fiber connections, THz transceivers may help further reduce the dimensions of THz spectroscopy and imaging systems.

Electro-optic crystal and photoconductive antenna embodiments of the THz transceiver of the present invention are discussed below in more detail. Also discussed is an exemplary tomography application for an electro-optic crystal transceiver.

A. Electro-Optic Crystal Transceiver

Figure 1:
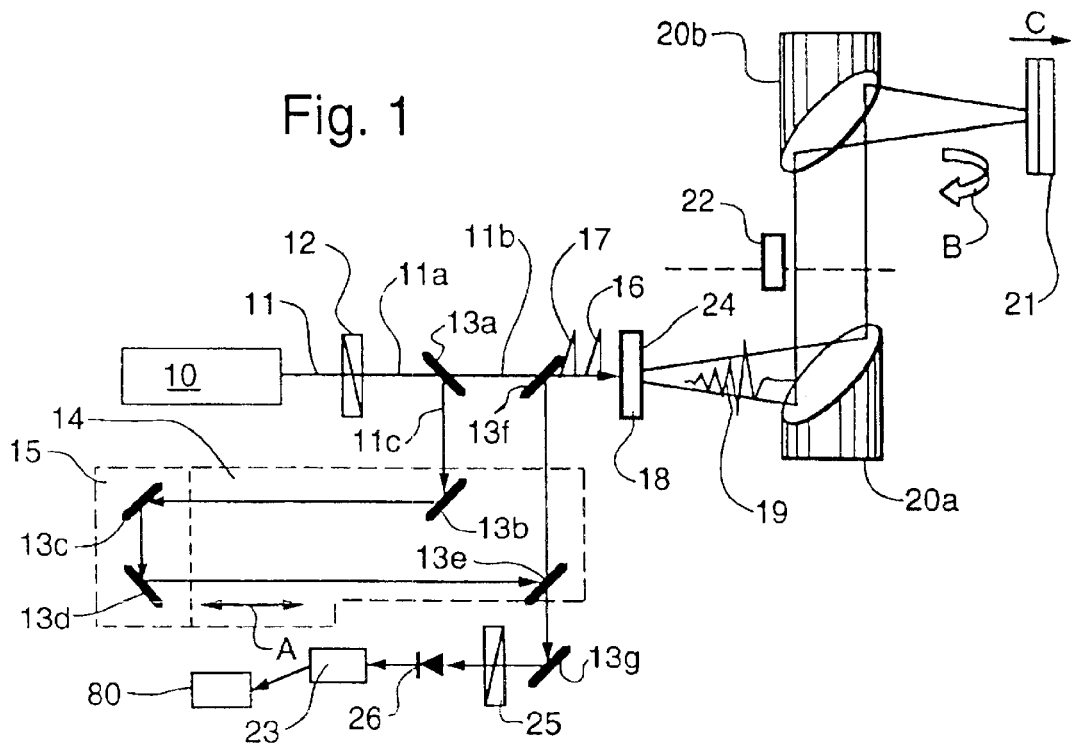
FIG. 1 is a schematic illustration of an exemplary setup incorporating an electro-optic crystal transceiver.

FIG. 1 shows an exemplary setup to demonstrate the functionality of an electro-optic crystal transceiver. A laser 10 generates an optical pulse which first travels along a path 11 to a polarizer 12. Polarizer 12 is optional. The polarized pulse moves along a path 11a and hits a beam-splitter 13a, which transmits a portion of the pulse as a pump pulse along a path 11b, and reflects a portion of the pulse as a probe pulse along a path 11c. The probe pulse traveling along path 11c is bounced off of mirror 13b, then off of mirrors 13c and 13d in movable stage 15, and then bounced off of beam-splitters 13e and 13f. Movable stage 15 is movable back and forth along arrow A. Delay stage 14, of which movable stage 15 is a component, thus provides a variable delay between a pump pulse 16 and a probe pulse 17. Artisans often refer to delay stage 14 as a Michaelson interferometer.

Pump pulse 16 first illuminates an electro-optic (EO) crystal 18, which generates a THz pulse 19 via optical rectification. A mechanical chopper 22 modulates THz pulse 19. THz pulse 19 is collimated by one or more parabolic mirrors 20a and 20b and reflected off a sample 21 (as indicated by arrow B). Probe pulse 17 samples the reflected THz signal via the electro-optic effect in EO crystal 18, where the phase of the probe pulse is modulated by the reflected THz pulse. The probe pulse then reflects from a back surface 24 of EO crystal 18, and is reflected from a beam-splitter 13f, transmitted through a beam-splitter 13e, and reflected from a mirror 13g, through an optical analyzer (polarizer) 25 and detected by a photodetector 26. Polarizer 25 transfers the phase variation in the probe pulse induced by the reflected terahertz pulse to an intensity variation that can be detected by photodetector 26. Lock-in amplifier 23, having its reference input (not shown) connected to the clock output (not shown) of chopper 22 so that its frequency is auto-locked to the frequency of the chopper, extracts the desired signal from background noise.

A data processor 80, such as a computer containing data processing software, may comprise any single unit or multiple processing units that process, store, or both process and store the output signal from lock-in amplifier 23. Data processor 80 may produce, for example, an image of sample 21 based upon the intensity or time-delay of the reflected terahertz pulses. This function is discussed further below.

The number of mirrors 13*a*–*g* and 20*a,b* can be varied as desired to address the physical needs of the particular setup desired. For example, only a single mirror 20*a* may be used for collimation, with the sample 21 placed in the position where mirror 20*b* is shown in FIG. 1. In another embodiment, no mirror at all may be used. Also, instead of using a Michaelson interferometer, probe pulse 17 may be generated by any other method known in the art to provide a probe pulse synchronized with pump pulse 16.

In one exemplary embodiment, a regenerative amplified Ti:sapphire laser (such as a Coherent Rega 9000), having a 800 nm, 180 fs pulse duration and a 250-kHz repetition rate, was used to generate the pulses. Electrooptic crystal 18 was a 4.5-mm thick <110> oriented ZnTe crystal. The average power of pump pulse 16 and probe pulse 17 was about 105 mW, and chopper 22 modulated the terahertz pulse at 450 Hz. The relatively low modulation frequency was provided by the use of a relatively wide (for example about 2 cm) slot chopper blade to match the relatively large size of the THz pulse. Lock-in amplifier 23 had a 300 ms integration time.

The polarization direction of the optical probe pulse was parallel to that of the optical pump pulse, and optical polarizer 25 (analyzer) was oriented perpendicular to the polarization provided by input polarizer 12 for better rejection of the pump pulse and for cross-balance detection of the probe pulse. The optimum orientation of the pump pulse polarization (as predicted by a theoretical calculation) was preferably about 25.7° counter-clockwise from the (001) z-axis of the (110) ZnTe crystal, and the polarization of the generated THz field was about 77° counter-clockwise from the z-axis. Other orientations may also be used.

Figure 2:
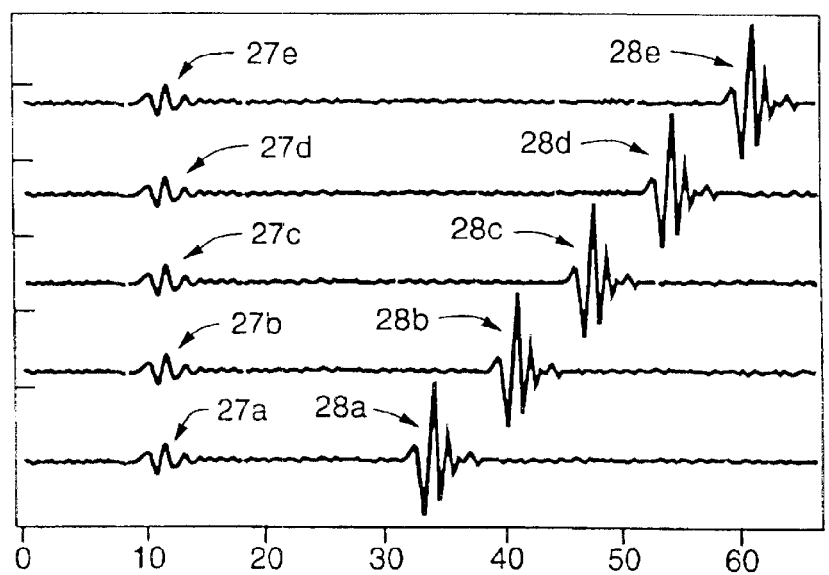
FIG. 2 is a plot of exemplary waveforms generated using the setup of FIG. 1.

FIG. 2 shows a set of waveforms measured by using a metallic mirror as sample 21 and moving it along the THz propagation direction in the direction of arrow C with a 1 mm step (6.6 ps round trip time). The first signals 27*a*–*e* shown in FIG. 2 are the THz reflections from the metallic chopper blade, which was set to be substantially perpendicular to the propagation direction of the THz pulse. The time positions of the first signals 27*a*–*e* are therefore fixed. The second signals 28*a*–*e* are the reflected THz signals from the metallic mirror. The positions of the second signals shift with the location of the mirror.

The time delay between two THz signals is the round trip time of a THz pulse traveling between the chopper and the metallic mirror. The reflection from the chopper blade automatically serves as a reference marker for the system calibration. There is a π phase difference between the phases of the reflected signals from the chopper and from the metallic mirror after the chopper, arising from the phase difference between the THz pulses transmitted and reflected by the chopper. Therefore, these two signals measured with the lock-in amplifier show opposite polarities. The time delays between second signals 28*a*–*e* and first signals 27*a*–*e* in FIG. 2 demonstrate the suitability of the present invention for tomography.

Subject to there being cross-balance detection with the parallel optical pump and probe polarization, the overall efficiency of the electro-optic THz transceiver is about 50% smaller than for a transmitter and receiver used separately. Both the theoretical calculations and experimental results show that operation with a pump:probe power ratio of 1:1 is optimal. The results shown in FIG. 2 indicate a peak-to-peak current for the THz signal of about 1.8 nA and a noise floor of about 6.8 pA, providing a dynamic range of about 270. The dynamic range may be varied dependent upon the chopper modulation frequency and precision of the pulse alignment. For example, higher modulation frequencies may provide a greater dynamic range than lower modulation frequencies.

Figure 3:
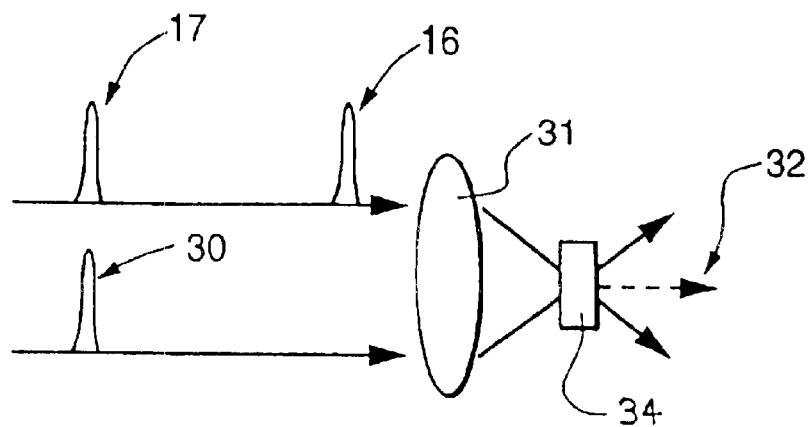
FIG. 3 shows a partial schematic illustration of an exemplary noise-reduction apparatus for an electro-optic crystal transceiver embodiment.

Because the pump and probe pulses are collinear, the electro-optic transceiver has an optical background due to the presence of the reflected pump laser pulse. Although a large optical background added to the probe pulse may impact system performance, such as by lowering the signal-to-noise ratio, there are several methods available to mitigate or eliminate the impact of the optical background. One method is to use the different timing of pump pulse 16 and probe pulse 17 to discriminate the pump pulse background. For example, as shown in FIG. 3, a lens 31 may be positioned before a crystal 34, such as beta-barium borate (BBO). A gate pulse 30 is used to generate a background-free second harmonic signal 32 with the probe pulse reflected from the transceiver. The combination of lens 31 and crystal 34 may be placed between polarizer 25 and photodetector 26 in the setup shown in FIG. 1. The second harmonic signal carries the probe pulse modulation by the THz field without the presence of the pump pulse background. This configuration may increase the noise level from the laser noise, however, because laser noise is amplified during generation of the second harmonic signal. Therefore, this method is suited for a system with a very quiet laser source.

B. Photoconductive Antenna Transceiver

Figure 4:
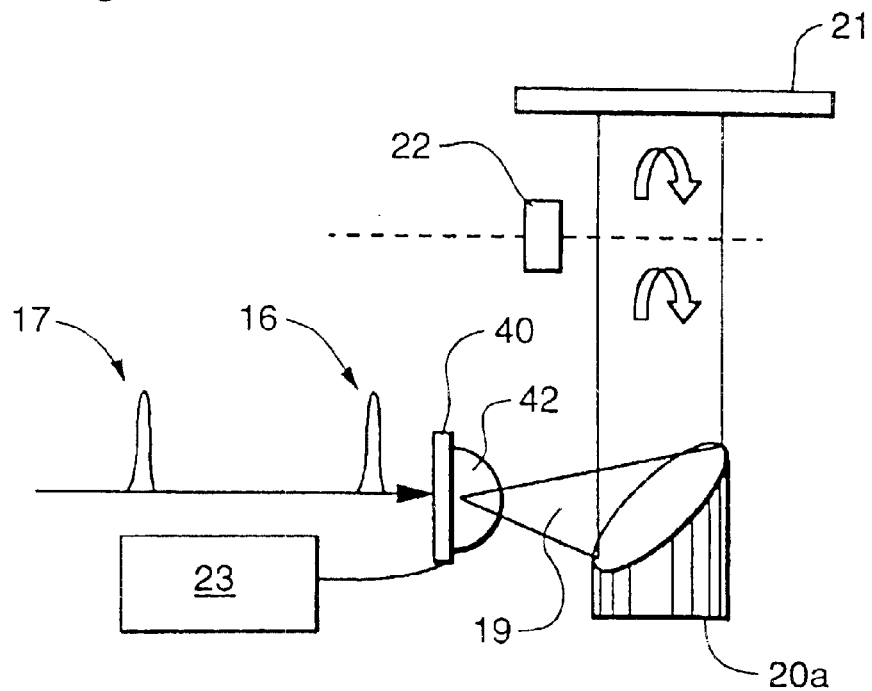
FIG. 4 is a schematic illustration of an exemplary setup incorporating a photoconductive antenna transceiver.

FIG. 4 shows a portion of an exemplary setup to demonstrate the functionality of a photoconductive antenna as a transceiver. The laser source and delay stage portions are similar to the setup shown in FIG. 1 and thus are not repeated in FIG. 4. FIG. 4 picks up where the pair of synchronized optical pulses—pump pulse 16 and probe pulse 17—illuminate a photoconductive dipole antenna 40. Dipole antenna 40 is biased with a power source (not shown, typically a DC source such as a battery) and attached to a lens 42.

Pump pulse 16 launches THz pulse 19 by exciting dipole antenna 40. THz pulse 19 is collimated by parabolic mirror 20*a* and reflected by sample 21. To isolate the interference of the pump-pulse-induced photo-current, mechanical chopper 22 modulates the THz pulse. Probe pulse 17 samples the reflected THz signal using dipole antenna 40. The simultaneous arrival of the reflected THz signal and probe pulse 17 at dipole antenna 40 induces a current between the electrodes (not shown) of the antenna that is proportional to the THz electric field. Lock-in amplifier 23 detects this current. Electronics downstream of the lock-in amplifier 23 (for example, data processor 80 as shown in FIG. 1) may be the same for a photoconductive antenna transceiver system as for an electro-optic crystal transceiver system.

Because both pump pulse 16 and probe pulse 17 illuminate the same photoconductor, they induce current in the same way. Only the current associated with probe pulse 17, however, is modulated by THz pulse 19. The photocurrent associated with the power source (typically a DC field) is not modulated, and lock-in amplifier 23 may therefore filter it out so that the signal may be extracted. Pump pulse 16 and probe pulse 17 are typically identical except for their relative timing. Whichever pulse is generated earlier serves as the pump pulse.

In one exemplary embodiment, a Ti:sapphire laser with 800 nm center wavelength, 120 fs laser pulses, and a 86 MHz repetition rate was used as the optical source, and the average power for the pump and probe pulses was 20 mW. Antenna 40 was low-temperature-grown GaAs, 50 μm long, biased with a 9V battery, and attached to a silicon lens 42. Chopper 22 modulated the THz pulse at 453 Hz, and sample 21 was a metallic mirror. The measured THz waveform had a signal-to-noise ratio (SNR) of about 200.

Figure 5:
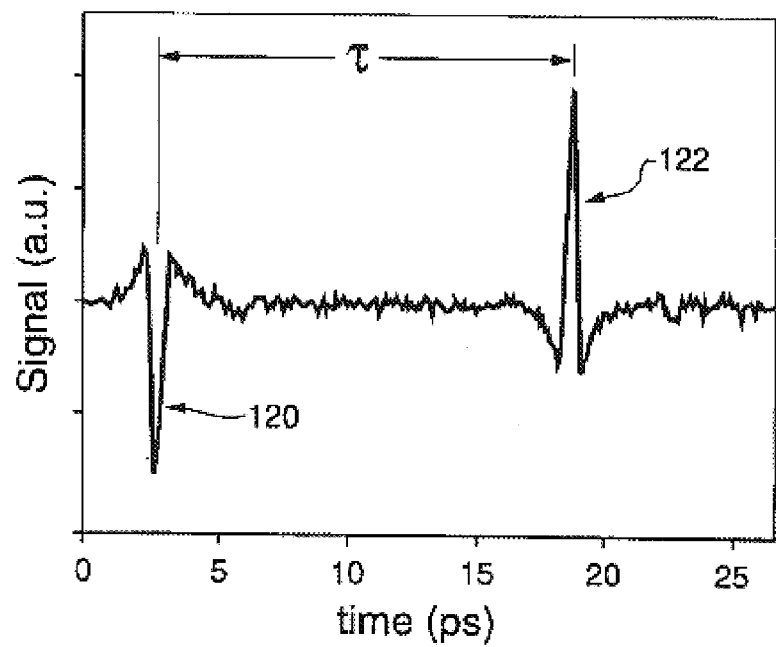
FIG. 5 is a plot of an exemplary measured temporal waveform using the setup of FIG. 4.

FIG. 5 shows a plot of an exemplary measured temporal waveform of the THz signal generated by the system shown in FIG. 4. A first signal 120 is the THz reflection from the metallic chopper blade, with the chopper blade set essentially perpendicular to the propagation direction of the THz pulse. A second signal 122 is the THz signal transmitted through the chopper and reflected back from the metallic mirror. As shown in FIG. 5, there is a π phase difference between the first and second signals as measured with the lock-in amplifier 23, resulting in opposite polarities. The time delay τ between two THz signals is the round-trip time of a THz pulse travelling between chopper 22 and metallic mirror sample 21. The reflection from the chopper blade automatically serves as a reference marker for system calibration.

The photocurrent generated by the pump pulse, probe pulse, and bias voltage contribute to noise in the system shown in FIG. 5. The signal-to-noise ratio may be dependent at least in part upon the filtering circuit and operational conditions, such as the chopper modulation frequency. Increasing the modulation frequency, for example to 2–3 kHz, may provide a better signal-to-noise ratio because the noise density decreases for higher frequencies.

C. Tomographic Imaging

THz transceivers enable tomographic THz imaging in a reflection geometry in which THz pulses are reflected from different layers of metal objects. The time delay of these pulses is used to construct a tomographic image. Data processor 80, as shown in FIG. 1 receiving signals from lock-in amplifier 23, is used to produce the tomographic images of imaged objects based upon the time-delayed terahertz signals. Data processors, such as computers with corresponding software, for producing tomographic images based upon time delays in electromagnetic pulses are generally known in the art, and data processor 80 may be any such known device.

As discussed above, the working efficiency of an electro-optic transceiver constructed by a (110) zinc-blend crystal is optimized when the pump pulse polarization is about 25°–26° counter-clockwise from the crystallographic z-axis of the crystal. The setup shown in FIG. 1 may be used for a THz tomographic imaging system with an electro-optic transceiver. Use of a transceiver in accordance with the method of the present invention, rather than a separate transmitter and receiver, enables normal incidence of the THz pulse on the sample.

Figure 8:
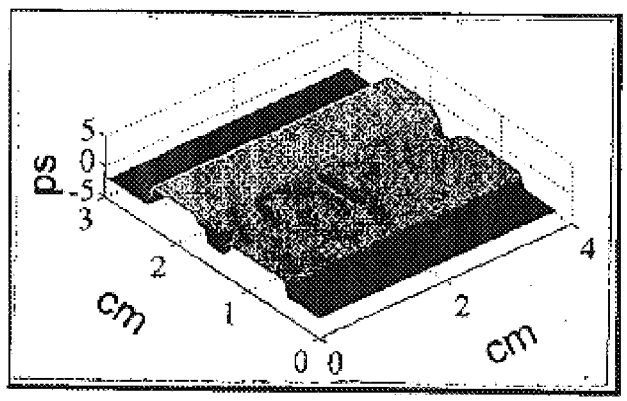
FIG. 8 is a tomographic image of the razor blade of FIG. 6 generated using an exemplary embodiment of the present invention, where the gray level on the z-axis represents the timing of the peak amplitude in picoseconds and the x-axis and y-axis units are in centimeters.
Figure 9:
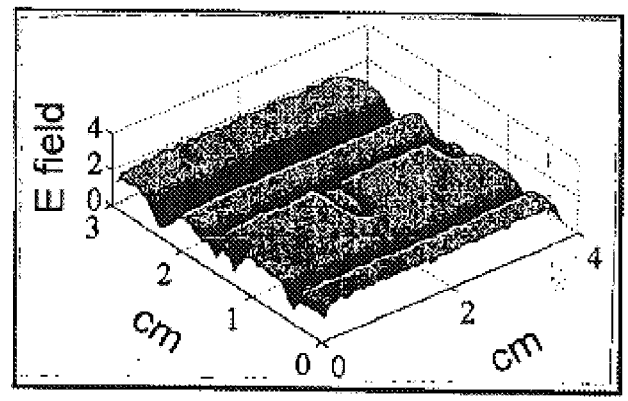
FIG. 9 is an image of the razor blade of FIG. 6 generated using an exemplary embodiment of the present invention, where the gray level on the z-axis represents the peak amplitude intensity and the x-axis and y-axis units are in centimeters.
Figure 6:
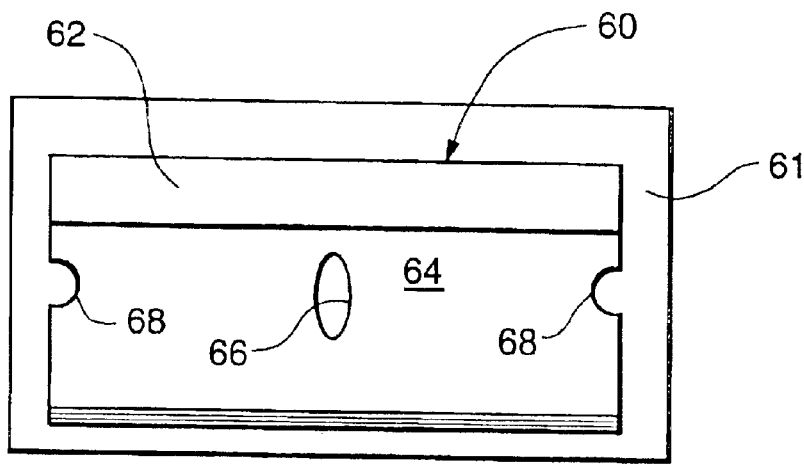
FIG. 6 is an illustration of a common razor blade as known in the prior art.
Figure 7:
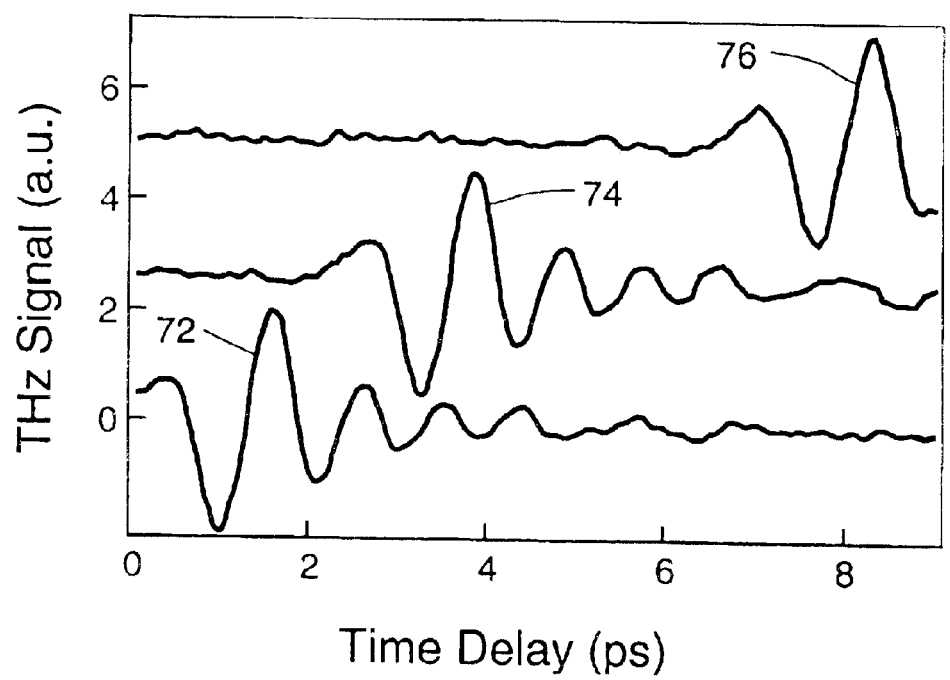
FIG. 7 is an illustration of a plot of the THz waveforms reflected from different layers of the razor blade of FIG. 6.

THz tomographic imaging using the electro-optic transceiver was demonstrated by imaging a razor 60, such as illustrated in FIG. 6, pasted on a metal mirror 61, with the razor-mirror combination used for sample 21 in the setup shown in FIG. 1. FIG. 7 shows the THz waveforms reflected from the three different reflection metal layers in the sample: a peak 72 from the metal handle 62 of razor 60, a peak 74 from the razor surface 64, and a peak 76 from the underlying metal mirror 61, such as reflected through the holes 66 or 68 in razor surface 64. The timing difference of the peak intensity indicates the spatial separation of those layers. The timing difference may be used to construct a three-dimensional tomographic image of a razor, as shown in FIG. 8. When the THz pulse is incident on the boundary of the different metal layers, only part of it can be reflected back and detected, decreasing the peak THz intensity. Thus, the peak intensity distribution can also form a THz image that indicates the profile of the object, as shown in FIG. 9.

The capabilities of the exemplary imaging system shown in FIG. 1 were demonstrated by creating THz tomographic images of an American quarter dollar and a British fifty pence piece, as shown in FIGS. 10A and 10B, respectively. Image contrast is affected by the THz pulse focal size and the flatness of the background metal surface. Where the background surface is not particularly flat, the image can be displayed in terms of the peak intensity within a certain short timing window to get some additional information on the imaged object, as is shown in FIGS. 11A and 11B. The width of the short timing window is determined by the degree of deviation from flatness. If two imaging areas are on two different reflection layers and their spatial separation is large enough, the image may be displayed as shown in FIGS. 11A and 11B at two different timing positions as determined by the spatial separation. This method allows three-dimensional THz imaging without displaying the image based upon the timing of peak amplitude.

Imaging systems using electro-optic transceivers have spatial resolution on the order of millimeters and depth resolution on the order of sub-millimeters. Imaging of objects ten meters away, and even one hundred meters or more away depending on water vapor absorption, is feasible. Thus, terahertz transceivers may enable imaging of objects through walls or doors. For example, terahertz imaging may be used in law enforcement to detect the location of a terrorist, his weapon, and a hostage behind a closed door.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A system for emitting and detecting one or more terahertz frequency electromagnetic pulses, the system comprising:
   a single transceiver device for both emitting and detecting the pulses;
   an optical source and related optics for providing:
   (a) a plurality of pump pulses to excite the transceiver to emit a corresponding plurality of terahertz output pulses, and
   (b) a plurality of probe pulses timed to illuminate the transceiver simultaneously with a corresponding plurality of reflected terahertz pulses;
   a chopper for modulating the terahertz output pulses by alternately transmitting and reflecting the pulses at a first frequency, the chopper having a clock output and positioned between the transceiver and an object such that terahertz output pulses reflected by the chopper have a polarity opposite terahertz output pulses reflected by the object; and
   a lock-in amplifier, having a reference input connected to the chopper clock output and auto-locked to the first frequency, for receiving and reducing noise in a plurality of electrical signals, each signal carrying information proportional to a corresponding reflected terahertz pulse as detected by the transceiver.

2. The system of claim 1 wherein the single transceiver device comprises an electro-optic crystal.

3. The system of claim 2 wherein the electro-optic crystal is mounted to the end of an optical fiber.

4. The system of claim 3 wherein the optical fiber is a polarization-preserved optical fiber.

5. The system of claim 4 wherein the electro-optical crystal has a volume of less than about 1 mm$^3$.

6. The system of claim 1 wherein the single transceiver device comprises a photoconductive antenna.

7. The system of claim 1 further comprising one or more parabolic mirrors between the transceiver and the object.

8. The system of claim 1 wherein the transceiver comprises a photoconductive antenna that produces the electrical signals received by the lock-in amplifier, each electrical signal produced when a probe pulse and a reflected terahertz pulse simultaneously illuminate the antenna.

9. The system of claim 8 wherein the system further comprises a data processor for processing the noise-reduced output signal from the lock-in amplifier.

10. The system of claim 9 wherein the data processor is adapted to produce a tomographic image based upon a difference in time between the reflected pulses from different layers of the object.

11. The system of claim 9 wherein the data processor is adapted to produce an image based upon a peak amplitude of each of the reflected pulses.

12. The system of claim 1 wherein the transceiver comprises a electro-optic crystal that reflects a plurality of modulated probe pulses, each modulated probe pulse created when the probe pulse and reflected terahertz pulse simultaneously illuminate the transceiver and the terahertz pulse modulates the probe pulse, the system further comprising:
a photodetector for detecting the modulated, reflected probe pulses and for generating the plurality of electrical signals received by the lock-in amplifier, the electrical signals carrying information transmitted by the modulated, reflected probe pulses.

13. The system of claim 12 wherein the system further comprises a data processor for processing the noise-reduced output signal from the lock-in amplifier.

14. The system of claim 13 wherein the data processor is adapted to produce a tomographic image based upon a difference in time between the reflected pulses from different layers of the object.

15. The system of claim 13 wherein the data processor is adapted to produce an image based upon a peak amplitude of each of the reflected pulses.

16. A method for emitting and detecting a terahertz frequency electromagnetic pulse using a single transceiver device, the method comprising the steps of:
(a) exciting the transceiver device with a pump pulse to emit a first terahertz frequency output pulse;
(b) modulating the terahertz frequency output pulse with a chopper positioned between the transceiver device and an object to be illuminated with the modulated terahertz frequency output pulses, the chopper alternately transmitting and reflecting the pulses;
(c) illuminating the object with terahertz frequency output pulses transmitting by the chopper so that the object reflects terahertz pulses having an opposite polarity from terahertz pulses reflected by the chopper; and
(d) illuminating the transceiver device with a reflected terahertz pulse simultaneously as a probe pulse illuminates the transceiver device, such that the transceiver device produces first signal carrying information from the reflected terahertz pulse.

17. The method of claim 16 wherein the transceiver device is an electro-optic crystal, wherein step (d) comprises the terahertz pulse modulating the probe pulse in the electro-optic crystal and the electro-optic crystal reflecting the modulated probe pulse from a back surface of the electro-optic crystal, wherein the first signal comprises the reflected, modulated probe pulse, the method further comprising:
(e) detecting the reflected, modulated probe pulse with a photodetector and converting the information to a second signal; and
(f) reducing noise in the second signal with a lock-in amplifier to produce a third, noise-reduced signal.

18. The method of claim 17 further comprising:
(g) processing the third, noise-reduced signal with a data processor.

19. The method of claim 18 wherein the object comprises a plurality of layers, each layer a respective distance from the transceiver, the method comprising generating a plurality of pump pulses, probe pulses, and terahertz pulses such that the object reflects a plurality of reflected terahertz pulses, each reflected pulse having a peak amplitude intensity, the method further comprising:
(h) using information related to the peak amplitude intensity to generate an image of the object.

20. The method of claim 18 wherein the object comprises a plurality of layers, each layer a respective distance from the transceiver, the method comprising generating a plurality of pump pulses, probe pulses, and terahertz pulses such that the object reflects a plurality of reflected terahertz pulses, each reflected pulse having a peak amplitude timing, the timing corresponding to the distance of the layer that reflected the pulse from the transceiver, the method further comprising:
(h) using information related to the peak amplitude timing to generate an image of the object.

21. The method of claim 16 wherein the transceiver device is a photoconductive antenna, wherein step (d) comprises the terahertz pulse and the probe pulse creating a current in the antenna comprising the first signal, the method further comprising:
(e) reducing noise in the first signal with a lock-in amplifier to produce a second, noise-reduced signal.

22. The method of claim 21 further comprising:
(f) processing the second, noise-reduced signal from the lock-in amplifier with a data processor.

23. The method of claim 22 wherein the object comprises a plurality of layers, each layer a respective distance from the transceiver, the method comprising generating a plurality of pump pulses, probe pulses, and terahertz pulses such that the object reflects a plurality of reflected terahertz pulses, each reflected pulse having a peak amplitude intensity, the method further comprising:
(g) using information related to the peak amplitude intensity to generate an image of the object.

24. The method of claim 22 wherein the object comprises a plurality of layers, each layer a respective distance from the transceiver, the method comprising generating a plurality of pump pulses, probe pulses, and terahertz pulses such that the object reflects a plurality of reflected terahertz pulses, each reflected pulse having a peak amplitude timing, the timing corresponding to the distance of the layer that reflected the pulse from the transceiver, the method further comprising:
(g) using information related to the peak amplitude timing of the reflected terahertz pulse to generate an image of the object.

* * * * *

UNITED STATES PATENT AND TRADEMARK OFFICE
CERTIFICATE OF CORRECTION

PATENT NO. : 6,844,552 B2
DATED : January 18, 2005
INVENTOR(S) : Xi-Cheng Zhang et al.

It is certified that error appears in the above-identified patent and that said Letters Patent is hereby corrected as shown below:

<u>Column 1,</u>
Line 6, insert:
 -- The U.S. Government has a paid-up license in this invention and the right in limited circumstances to require the patent owner to license others on reasonable terms as provided for by the terms of Contract No. DE-F607-98 ER62706 awarded by the Department of Energy. --.

Signed and Sealed this

Twenty-third Day of August, 2005

JON W. DUDAS
*Director of the United States Patent and Trademark Office*